US012657731B2

(12) United States Patent
Qin et al.

(10) Patent No.: US 12,657,731 B2
(45) Date of Patent: *Jun. 16, 2026

(54) APPARATUS AND METHOD FOR IMAGE SEGMENTATION USING A DEEP CONVOLUTIONAL NEURAL NETWORK WITH A NESTED U-STRUCTURE

(71) Applicant: Exo Imaging, Inc., Santa Clara, CA (US)

(72) Inventors: Xuebin Qin, Edmonton (CA); Zichen Zhang, Edmonton (CA); Masood Dehghan, Edmonton (CA); Dornoosh Zonoobi, Edmonton (CA)

(73) Assignee: Exo Imaging, Inc., Santa Clara, CA (US)

( * ) Notice: Subject to any disclaimer, the term of this patent is extended or adjusted under 35 U.S.C. 154(b) by 412 days.

This patent is subject to a terminal disclaimer.

(21) Appl. No.: 18/494,660

(22) Filed: Oct. 25, 2023

(65) Prior Publication Data

US 2024/0135545 A1 Apr. 25, 2024
US 2024/0233133 A9 Jul. 11, 2024

Related U.S. Application Data

(63) Continuation of application No. 17/135,490, filed on Dec. 28, 2020, now Pat. No. 11,836,928.

(Continued)

(51) Int. Cl.
*G06T 7/143* (2017.01)
*G06N 3/08* (2023.01)
(Continued)

(52) U.S. Cl.
CPC ............... *G06T 7/143* (2017.01); *G06N 3/08* (2013.01); *G06N 7/01* (2023.01); *G06T 3/40* (2013.01);
(Continued)

(58) Field of Classification Search
CPC . G06T 7/143; G06T 3/40; G06T 2207/10132; G16H 30/40; G06N 7/01; G06N 3/08
See application file for complete search history.

(56) References Cited

U.S. PATENT DOCUMENTS

| | | | | |
|---|---|---|---|---|
| 10,592,820 B2 * | 3/2020 | Cao | ......................... | G06V 10/50 |
| 10,878,569 B2 * | 12/2020 | Akselrod-Ballin | .... | G16H 30/20 |

(Continued)

OTHER PUBLICATIONS

Zhou, Zongwei, et al, "UNet++: A Nested U-Net Architecture for Medical Image Segmentation" arXiv preprint arXiv: 1807.10165 (2018) (Year: 2018).*

(Continued)

*Primary Examiner* — Mohammed H Zuberi

(74) *Attorney, Agent, or Firm* — Morgan, Lewis & Bockius LLP

(57) ABSTRACT

A device receives an image. The image is applied to a sequence of encoders that includes a first encoder and one or more subsequent encoders, each including a U network encoder which performs convolution neural network processing. The one or more subsequent encoders receive a down-sampled version of the image from a prior encoder. The sequence of encoders form a first dimension orthogonal to the orthogonal dimension. A result of the sequence of encoders is applied to a sequence of decoders that includes a first decoder and one or more subsequent decoders. A respective decoder comprises a U network decoder that performs convolution neural network processing of an up-sampled version of the image from the first decoder. Probability outputs are produced from paired encoders and decoders in the sequence of encoders and the sequence of decoders. The probability outputs are combined to form a final output.

20 Claims, 8 Drawing Sheets

Related U.S. Application Data

(60) Provisional application No. 62/955,045, filed on Dec. 30, 2019.

(51) Int. Cl.
    G06N 7/01        (2023.01)
    G06T 3/40        (2006.01)
    G16H 30/40       (2018.01)

(52) U.S. Cl.
    CPC ...  G16H 30/40 (2018.01); *G06T 2207/10132*
        (2013.01); *G06T 2207/20076* (2013.01); *G06T*
            *2207/20084* (2013.01); *G06T 2207/30004*
                                                (2013.01)

(56)                References Cited

U.S. PATENT DOCUMENTS

| | | | | |
|---|---|---|---|---|
| 11,423,540 B2 * | 8/2022 | Heindl | .................... | G06N 3/09 |
| 11,823,800 B2 * | 11/2023 | Wujek | ................ | G06N 3/0464 |
| 11,875,892 B2 * | 1/2024 | El-Baz | ..................... | G06T 7/11 |

| | | | | |
|---|---|---|---|---|
| 2018/0218502 A1 * | 8/2018 | Golden | ................. | G06N 3/096 |
| 2019/0066847 A1 * | 2/2019 | Jung | ..................... | G16H 30/20 |
| 2019/0122360 A1 * | 4/2019 | Zhang | ................. | G06V 10/764 |
| 2019/0261945 A1 * | 8/2019 | Funka-Lea | ........... | G06T 15/205 |
| 2020/0074271 A1 * | 3/2020 | Liang | ................... | G06N 3/0464 |
| 2020/0184660 A1 * | 6/2020 | Shi | ........................... | G06T 7/30 |
| 2020/0226422 A1 * | 7/2020 | Li | ........................ | G06N 3/0464 |
| 2020/0311932 A1 * | 10/2020 | Hooper | .............. | G06F 18/2413 |
| 2021/0383538 A1 * | 12/2021 | Deasy | ................... | G06N 3/088 |
| 2023/0419642 A1 * | 12/2023 | Joshi | ..................... | G06V 10/82 |

OTHER PUBLICATIONS

Xia, Xide, and Brian Kullis, "W-net: A deep model for fully unsupervised image segmentation" arXiv preprint arXiv: 1711. 08506 (2017) (Year: 2017).*
Wu, Meihan et al, "ECNet: Efficient convolutional networks for side scan sonar image segmentation" Sensors 19.9 (2019) (Year: 2019).*
Li, Chongyi et al, "Nested Network with Two-Stream Pyramid for Salient Object Detection in Optical Remote Sensing Images" arXiv preprint arXiv: 1906.08462 (2019) (Year: 2019).*

* cited by examiner

APPARATUS AND METHOD FOR IMAGE SEGMENTATION USING A DEEP CONVOLUTIONAL NEURAL NETWORK WITH A NESTED U-STRUCTURE

CROSS-REFERENCE TO RELATED APPLICATION

This application is a continuation of U.S. patent application Ser. No. 17/135,490, filed Dec. 28, 2020, which claims priority to U.S. Provisional Patent Application Ser. No. 62/955,045, filed Dec. 30, 2019, each of which are incorporated herein by reference.

FIELD OF THE INVENTION

This invention relates generally to image processing. More particularly, this invention is directed toward image segmentation using a deep convolution neural network with a nested U-structure.

BACKGROUND OF THE INVENTION

In medical imaging, image segmentation aims to assign a label to every pixel in the image and identify the anatomical structures, such as organs or lesions. Based on the segmentation results, quantitative features such as shape, size and characteristics can be calculated to determine the category and severity of an abnormality. Therefore, the accuracy and precision of segmentation directly affects the performance of the quantitative analysis and diagnosis.

Accurate segmentation by manual labeling is a tedious and time-consuming task. Hence, there is a need for a well-designed automatic computer-based segmentation algorithm to greatly reduce the workload of busy radiologists and improve decision making.

Segmentation of ultrasound (US) images is more challenging compared to other imaging modalities such as computed tomography (CT), magnetic resonance imaging (MRI) and X-ray because (1) Image segmentation is strongly influenced by the quality of data and ultrasound images have low quality due to the speckle noise, low contrast, low signal to noise ratio (SNR) and artifacts inherent to ultrasound imaging modality;

(2) Ultrasound image acquisition process is highly orientation dependent and relies on the ability of the technician acquiring the image, and hence might result in inconsistent images with missing boundaries, large variations in anatomical structures, e.g. in shape, size, orientation, echo strength, etc.

Conventional segmentation methods such as active contour, graph cuts and watershed have been studied for decades. In recent years, with the development of deep learning, many deep convolutional neural networks are proposed for image segmentation. Compared to conventional methods, these deep learning methods improve the segmentation performance both in terms of accuracy and robustness.

Most of the current image segmentation deep learning architectures (in which each pixel is assigned a label) are adapted from the image classification networks architectures (in which the whole image is assigned to a label). These image classification networks are usually designed to have multiple stages connected by pooling (down-sampling) operations.

On one hand, these pooling operations are expected to down-sample the feature maps of their previous stages to lower resolutions and enable the extraction of larger scale features by subsequent stages. On the other hand, the down-sampled feature maps enable the design of networks with wider (more feature channels in each layer) and deeper (more layers) architectures under the GPU memory constraint. Image classification networks, in general, sacrifice the spatial resolution to achieve deeper architecture. This is motivated by the observation that global and semantic information obtained from deep low resolution feature maps is sufficient to provide the per image labeling in classification tasks.

During image segmentation each pixel has to be assigned one label. This means that high resolution, multi-scale information and deep architectures are all important to guarantee the segmentation performance.

There is a need for an efficient architecture to capture and fuse richer local and global contextual information for ultrasound image segmentation.

SUMMARY OF THE INVENTION

A non-transitory computer readable storage medium has instructions executed by a processor to receive an ultrasound image. The ultrasound image is applied to a sequence of encoders where each encoder in the sequence of encoders performs convolution neural network processing of a down-sampled version of the ultrasound image from a prior encoder, the sequence of encoders form a first dimension. The ultrasound image is applied to a transition encoder with an orthogonal dimension to the first dimension. The ultrasound image is applied to a sequence of decoders where each decoder in the sequence of decoders performs convolution neural network processing of an up-sampled version of the ultrasound image from a prior decoder, the sequence of decoders form a second parallel dimension to the first dimension. Encoder and decoder configurations and the first dimension, the orthogonal dimension and the second parallel dimension thereby define a nested U network architecture. Probability segmentation maps are produced from paired encoders and decoders in the sequence of encoders and the sequence of decoders. The probability segmentation maps are combined to form a final probability segmentation output.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

A network architecture for segmentation operations has the following characteristics. First, it is able to extract multi-scale multi-resolution contextual information regardless of the size of the input feature maps. Second, it comprises residual blocks at different stages that are able to capture and fuse both richer local and global contextual information in each stage without degrading feature map resolution. Third, it has a deep enough nested architecture that enables strong fitting capability without significantly increasing the computation and memory costs. Fourth, it has a modular and flexible architecture that can be easily re-configured for hardware settings with limited memory and computation constraints and/or training datasets with different sizes. Fifth, it outperforms state-of-the-art deep-learning based segmentation methods in terms of accuracy, robustness and qualitative measures of segmentation results.

The segmentation network gets an ultrasound image as an input and outputs labels for every pixel in the image, while identifying anatomical structures, organs or lesions. The network architecture is a two-level nested U-like structure, called $U^2$-Net, depicted in FIG. 1. The top level is an eleven stages U-structure: 6 encoding stages En_1 through En_6 followed by five decoding stages De_1 through De_5. Each encoder/decoder stage is filled by a Residual U-block (bottom level U-structure). That is, each encoder/decoder stage defines a U-structure and the collection of encoder/decoder stages define a large U-structure.

Figure 3:
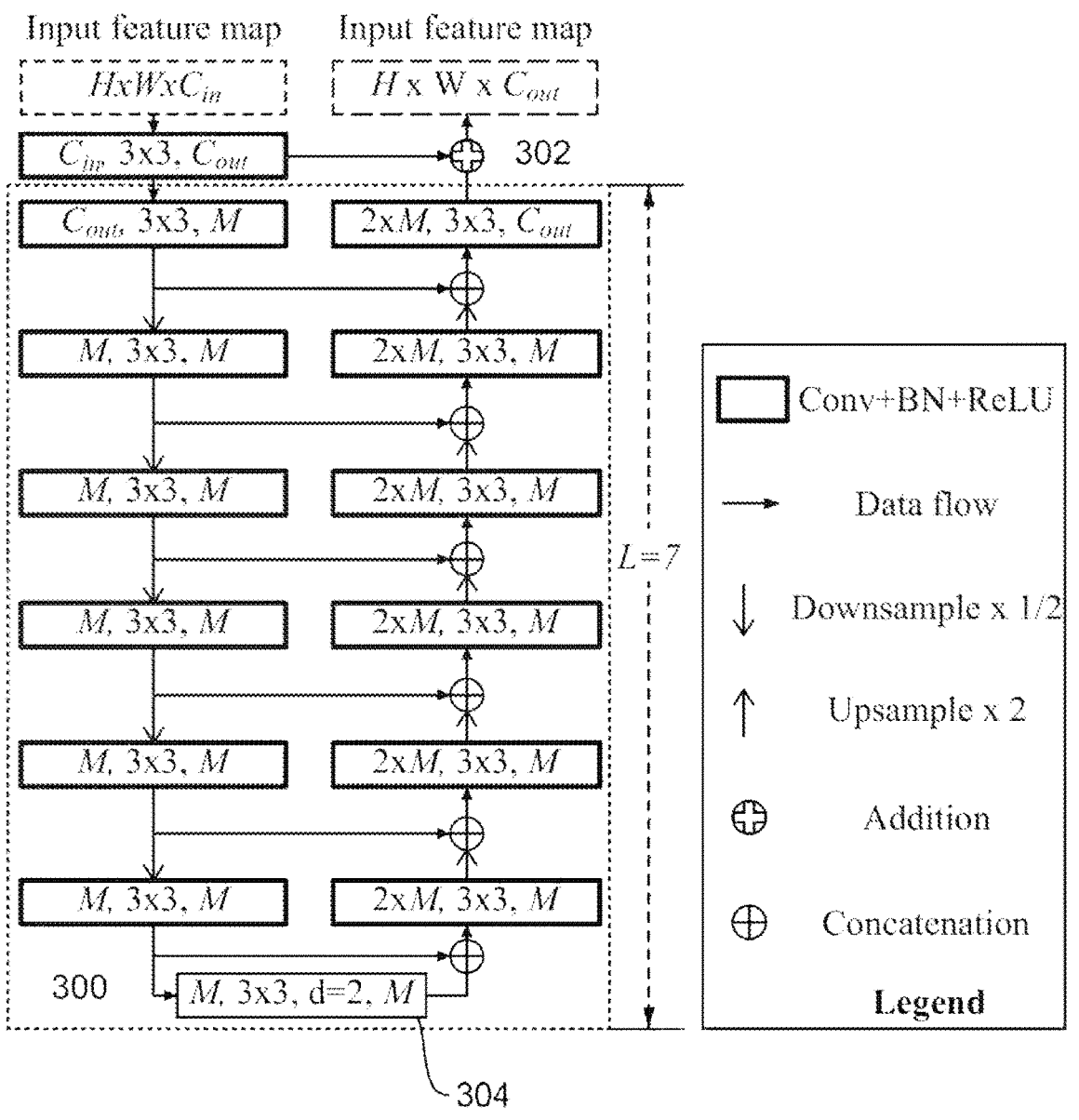
FIG. 3 illustrates a ReSidual U-block (RSU) network utilized in accordance with an embodiment of the invention.
Figure 4B:
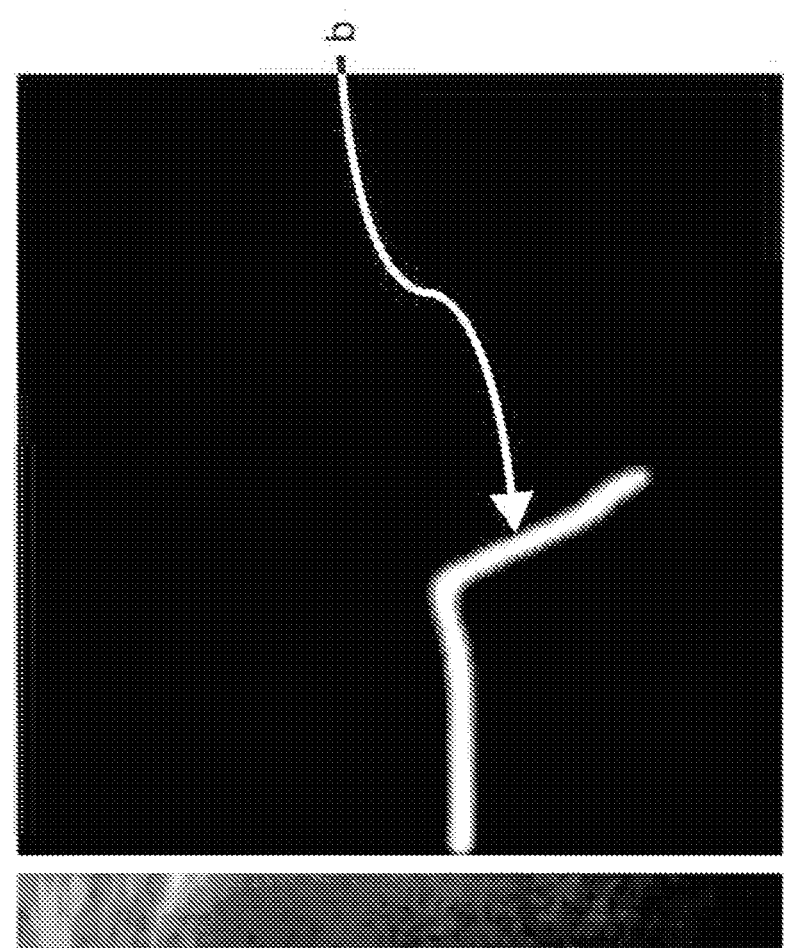
FIG. 4B illustrates a processed ultrasound image of the hip.
Figure 4A:
FIG. 4A illustrates an ultrasound image of a hip.
Figure 5B:
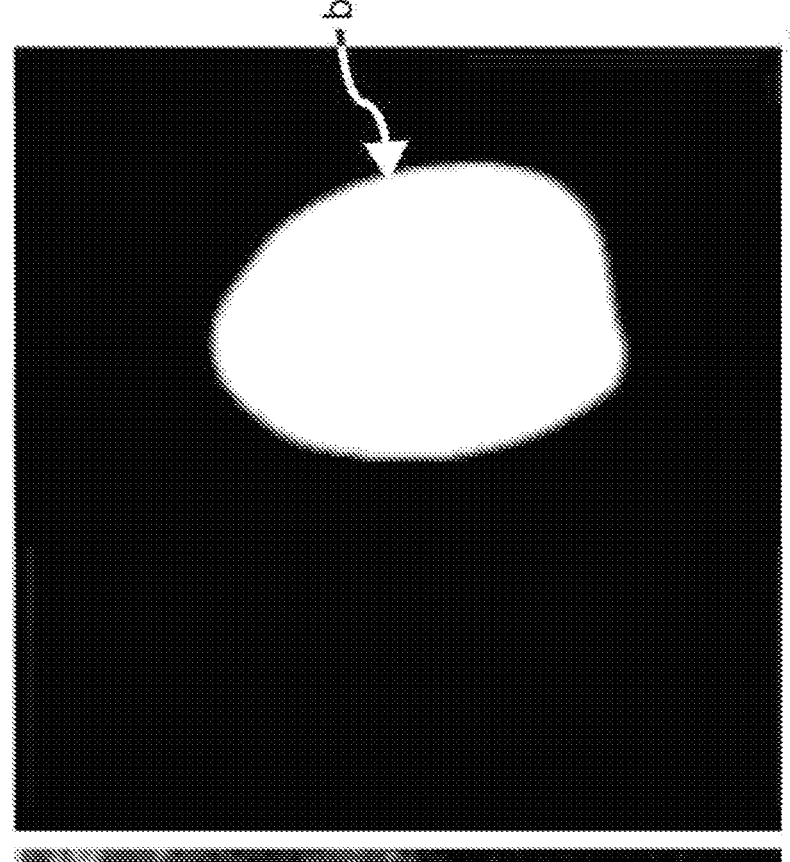
FIG. 5B illustrates a processed ultrasound image of the femoral head segmentation.
Figure 5A:
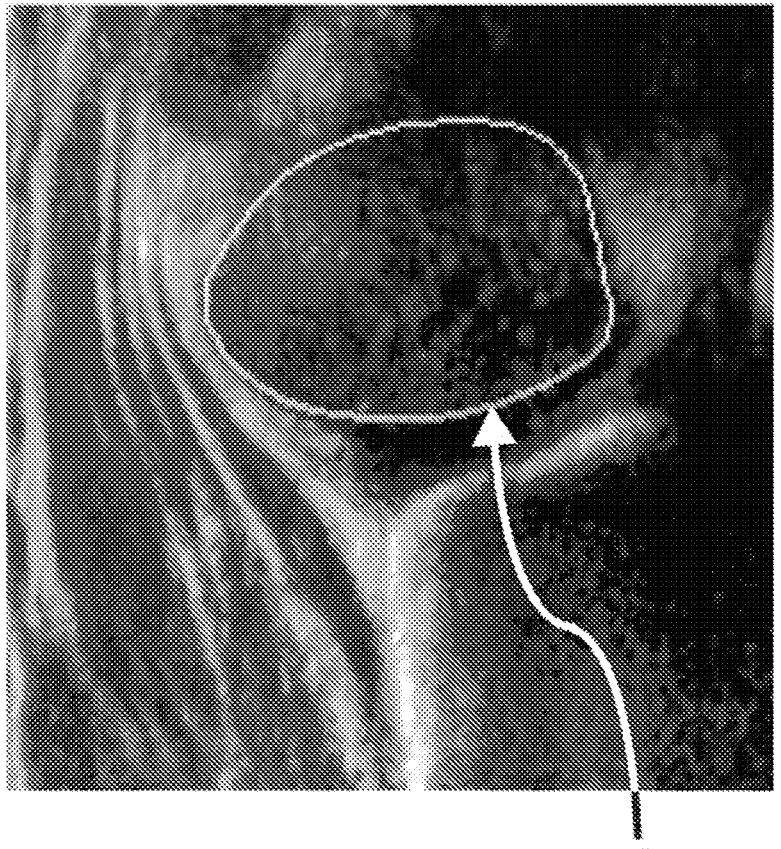
FIG. 5A illustrates an ultrasound image of a femoral head segmentation.

The detailed design of the Residual U-block (RSU) is shown in FIG. 3. The RSU block extracts multi-scale features by gradual down-sampling and recovers the resolution by gradually concatenating and up-sampling. The extracted multi-scale features are finally aggregated with the input feature maps by an addition operation, which is reflected by the residual connection design in RSU. The output of decoders and the last encoder stage generates six output probability maps S(1) through S(6) at different resolutions. These probability maps are then up-sampled to the input image size and are fused as shown with the addition sign in FIG. 1 to generate the segmentation probability map as the final output result of the network, shown as Sfuse/Segmentation output in FIG. 1.

Each stage is filled by a ReSidual U-block, which by itself is able to extract multi-scale context information from input feature maps with arbitrary resolutions (by configuring the height of the RSU). Further, the usage of RSU blocks in $U^2$-Net deepen the network architecture without significantly increasing the computation and memory costs because the input feature map of each RSU block is down-sampled to smaller resolution for larger scale feature extraction.

Figure 2:
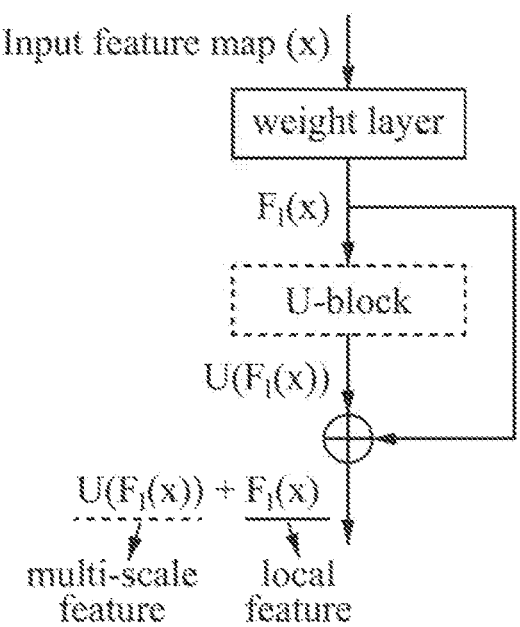
FIG. 2 illustrates a ReSidual U-block (RSU) processing component utilized in accordance with an embodiment of the invention.

FIG. 2 is an overview of the ReSidual U-block (RSU) with both local features $F_1(x)$ and multi-scale features extractors $U(F_1(x))$. The RSU gets x as the input feature map, a matrix with shape (batch_size, height, width, in_channels). $F_1(x)$ is the intermediate local feature map, a matrix with shape (batch_size, height, width, out_channels), extracted by a convolution operation $F_1$=conv(x,w1), where w1 indicates the convolution filter with shape (in_channels, 3, 3, out_channels). $U(F_1(x))$ is the output feature map, a matrix with shape (batch_size, height, width, out_channels), extracted by the U-block, which is a U-Net like symmetric encoder-decoder structure, from the intermediate feature map $F_1(x)$. The final output of RSU block is $F_{out}(X)=F_1(x)+U(F_1(x))$.

Turning to FIG. 3, the ReSidual U-block is built upon the combination of the residual connection and the U-Net like structure. The highlighted rectangle 300 contains the U-structure design that extracts multi-scale features. The residual connection 302 is introduced to fuse the local and multi-scale features in the input feature map resolution. This structure can be configured to extract multi-scale features from input feature maps with arbitrary resolutions by using different heights (L) of the U-structure.

Details of the ReSidual U-block: RSU-L($C_{in}$, M, $C_{out}$) include:

H: the height of the input feature map

W: width of the input feature map $C_{in}$: the channel number of the input feature map M: the channel number of the intermediate feature maps generated in the U-structure $C_{out}$: the channel number of the output feature map d: the dilation rate of the convolution filter, d=2 in the bottom block 304 indicates the dilation rate is set to 2.

L: the height of the U-structure, larger L leads to deeper RSU, more pooling operations, larger range of receptive fields and richer local and global features.

The invention provides a two-level nested U-structure deep network, called $U^n$-Net (n=2), that can be used for image segmentation. The exponential notation refers to nested U-structure rather than cascaded stacking. Theoretically, the exponent n can be set as an arbitrary positive integer to achieve single-level or multi-level nested U-structure. But architectures with too many nested levels will be too complicated to be implemented and employed in real-world applications. Here, we set n as 2 to build our two levels nested U-structure, $U^2$-Net. However, n may be set to 3 to provide a three-level nested U-structure deep network called $U^n$-Net (n=3), that can be used for image segmentation.

The architecture of $U^2$-Net has three parts: (a) a six-stages encoder, (b) a five-stages decoder and (c) a fusion module attached to the decoder stages and the last encoder stage. In encoder stages En_1, En_2, En_3 and En_4, we use Residual U-blocks (RSU) namely RSU-7, RSU-6, RSU-5 and RSU-4, respectively. The parameter "7", "6", "5" and "4" denote the height L of RSU blocks (see FIG. 3). The parameter L is usually configured according to the spatial resolution of the input feature maps. For feature maps with large height and width, we could use greater L to capture more large scale information. The resolution of feature maps in En_5 and En_6 are relatively low, further down-sampling of these feature maps leads to loss of useful context. Hence, in both En_5 and En_6 stages, RSU-4F are used, where "F" means that the RSU is a dilated version, in which we replace the pooling and up-sampling operations with dilated convolutions. That means all intermediate feature maps of RSU-4F have the same resolution with its input feature maps.

The decoder stages have similar structures to their symmetrical encoder stages with respect to En_6. For example, De_5 uses the dilated version residual U-block RSU-4F which is similar to that used in the encoder stages En_5. Each decoder stage takes the concatenation of the up-sampled feature maps from its previous stage and those from its symmetrical encoder stage as the input (see down-sampling and up-sampling arrows in FIG. 1).

The last part is the fusion module which is used to generate segmentation probability maps. Our $U^2$-Net first generates six side output saliency probability maps $S^6_{side}$, $S^5_{side}$, $S^4_{side}$, $S^3_{side}$, $S^2_{side}$ and $S^1_{side}$ from stages En_6, De_5, De_4, De_3, De_2, De_1 by a 3×3 convolution layer and a sigmoid function. Then, it up-samples these saliency maps to the input image size and fuses them with a concatenation operation followed by a 1×1 convolution layer and a sigmoid function to generate the final saliency probability map $S_{fuse}$ as follows:

$$S_{fuse}=\text{Sigmoid}(W(\text{concat}(S^6_{side},S^5_{side},S^4_{side},S^3_{side}, S^2_{side},S^1_{side})))$$

where W denotes the convolution operation with 1×1 filter.

Figure 1:
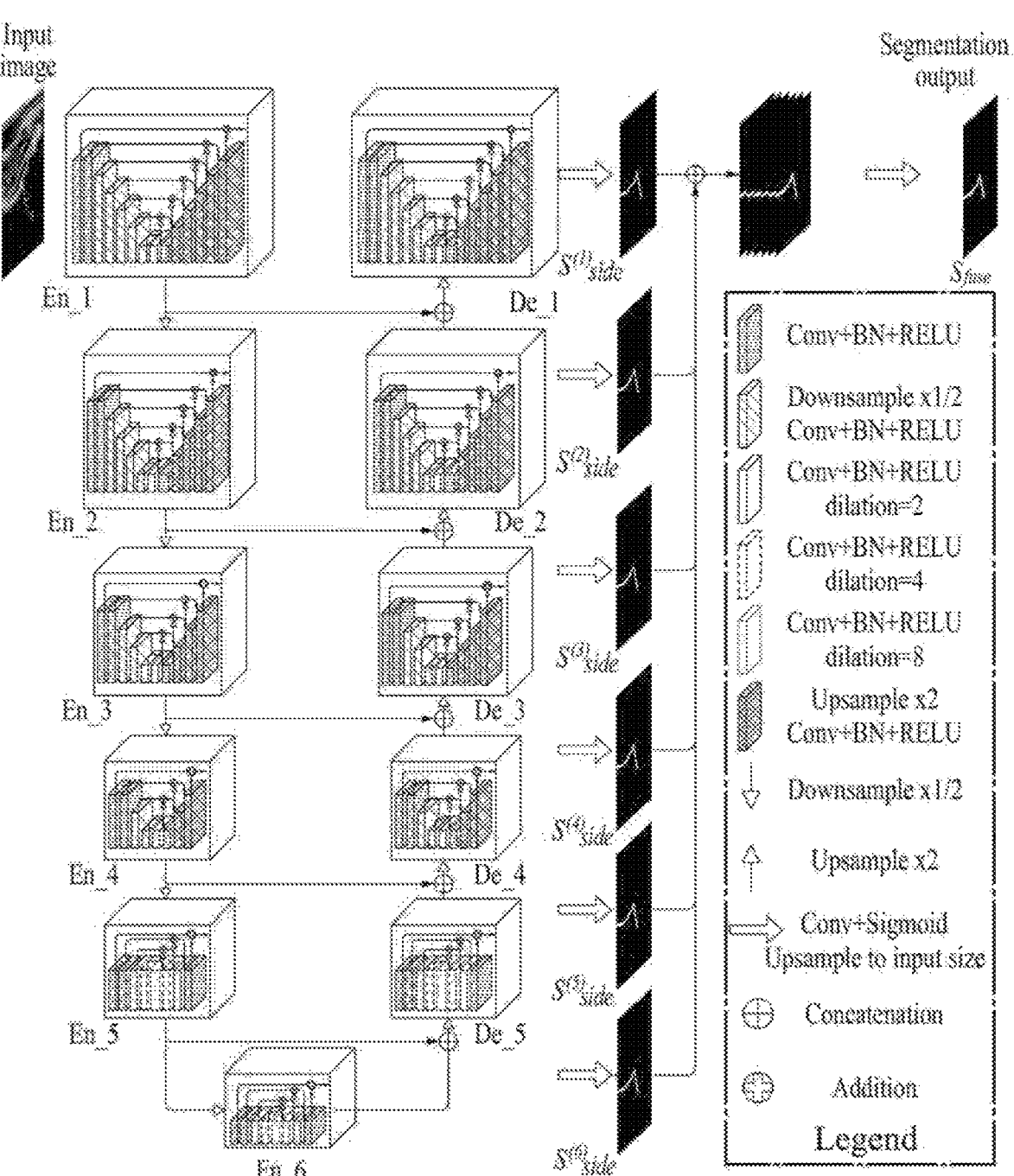
FIG. 1 illustrates an encoding and decoding architecture utilized in accordance with the invention.

Returning to FIG. 2, an input convolution layer transforms the input feature map x of size (H×W×$C_{in}$) to an intermediate map $F_1(x)$ with channel of $C_{out}$. This is a plain convolutional layer for local feature extraction. A U-Net like symmetric encoder-decoder structure with height of L (highlighted rectangle 300 in FIG. 3) takes the intermediate feature map $F_1(x)$ as input and learns to extract and encode the multi-scale contextual information $U(F_1(x))$. U represents the U-Net like structure as shown in FIG. 1. Larger L leads to deeper RSU, more pooling operations, larger range of receptive fields and richer local and global features. Configuring this parameter enables extraction of multi-scale features from input feature maps with arbitrary spatial resolutions. The multi-scale features are extracted from gradually down-sampled feature maps and encoded into high resolution feature maps by progressive up-sampling, concatenation and convolution. This process mitigates the loss of fine details caused by direct up-sampling with large scales. A residual connection 302 in FIG. 3 fuses local features and the multi-scale features by the summation: $F_1(x)+U(F_1(x))$.

The proposed network design has the following advantages: (a) it enables extracting multi-scale features from the down-sampled feature maps, (b) has a deeper architecture than the parallel multi-scale designs like inception blocks and pyramid pooling blocks, (c) allows increasing the depth of the whole architecture without significantly increasing the computational cost, (d) the architecture is modular and can be adapted to different computational environments. Given the architecture design of our RSU and $U^2$-Net, countless models can be instantiated by assigning different RSU heights and convolutional filter numbers. As an example, we provide a light and computationally efficient model instance (suitable to be used in mobile devices with limited computational memory). This model requires only 4.7 MB of memory to store the weights. For comparison, other state-of-the-art segmentation models require much larger memory (ten to hundred times more).

Detailed configurations of our light model is provided in Table 1. It is worth noting that Table 1 just shows one efficient model instance. The RSU blocks' heights and filter numbers can be easily changed to have a trade-off between model size and performance on different training dataset and working environments.

TABLE 1

| Details of a computationally efficient model instanced suitable for mobile devices | |
| --- | --- |
| Stages | Configurations RSU - L($C_{in}$, M, $C_{out}$) |
| En_1 | RSU - 7(1, 16, 64) |
| En_2 | RSU - 6(64, 16, 64) |
| En_3 | RSU - 5(64, 16, 64) |
| En_4 | RSU - 4(64, 16, 64) |
| En_5 | RSU - 4F(64, 16, 64) |
| En_6 | RSU - 4F(64, 16, 64) |
| De_5 | RSU - 4F(128, 16, 64) |
| De_4 | RSU - 4(128, 16, 64) |
| De_3 | RSU - 5(128, 16, 64) |
| De_2 | RSU - 6(128, 16, 64) |
| De_1 | RSU - 7(128, 16, 64) |

$U^2$-Net segmentation network learns a mapping function F, that transforms the input image $X_{input}$ with shape of (height,width,channel) into a segmentation mask $Y_{output}$ with shape of (height,width,1). More specifically, given an ultrasound image $X_{input}$ of shape (height, width, channel), the $U^2$-Net transforms the input $X_{input}$ to $Y_{output}=F(W, X_{input})$, where $Y_{output}$ is a probability map (pixel values in the range of [0,1]) with the shape of (height, width) and W denotes the weights of kernel filters. The choice of architecture design of $U^2$-Net determines the function F while its weights W are to be learned during the training process. The usage of the $U^2$-Net mainly requires two steps: (1) training, (2) inference. In the training process, given a set of ultrasound images $X_{train}$ and their corresponding annotated ground truth masks $Y_{train}$, the network weights W is determined by iteratively minimizing the cross entropy loss $L_{sum}$ between $Y_{train}$ ($S_{fuse}$, $S^6_{side}$, $S^5_{side}$, $S^4_{side}$, $S^3_{side}$, $S^2_{side}$ and $S^1_{side}$) and the estimated Y' train=$F(W,X_{train})$. The objective loss $L_{sum}$ is the summation of the cross entropy losses of the six side outputs and the fuse output:

$$L_{sum}=L_{fuse}+L^6_{side}+L^5_{side}+L^4_{side}+L^3_{side}+L^2_{side}+L^1_{side}.$$

where L denotes the binary cross entropy loss between the output probability maps ($S_{fuse}$, $S^6_{side}$, $S^5_{side}$, $S_{side}$, $S^3_{side}$, $S^2_{side}$ and $S^1_{side}$) and the ground truth mask. At the end of the training process the weights W are known.

In the inference process, given an ultrasound images $X_{inference}$, the trained network will produce the probability maps $Y_{inference}=F(W, X_{inference})$ based on the optimal weights W obtained from the training process. Although $Y_{inference}$ contains seven probability maps ($S_{fuse}$, $S^6_{side}$, $S^5_{side}$, $S^4_{side}$, $S^3_{side}$, $S_{side}$ and $S^1_{side}$). $S_{fuse}$ is taken as the final output of our network.

Sample segmentation results of the trained network (with parameters in Table 1) are shown in FIGS. 4 to 7 for different types of ultrasound images. FIG. 4A is an original ultrasound image; FIG. 4B is the processed output. Similarly, FIG. 5A is an original ultrasound image; FIG. 5B is the processed output. The images display a hip where acetabulum bone segmentation is shown in FIGS. 4A and 4B and femoral head segmentation is shown in FIGS. 5A and 5B.

Figure 6B:
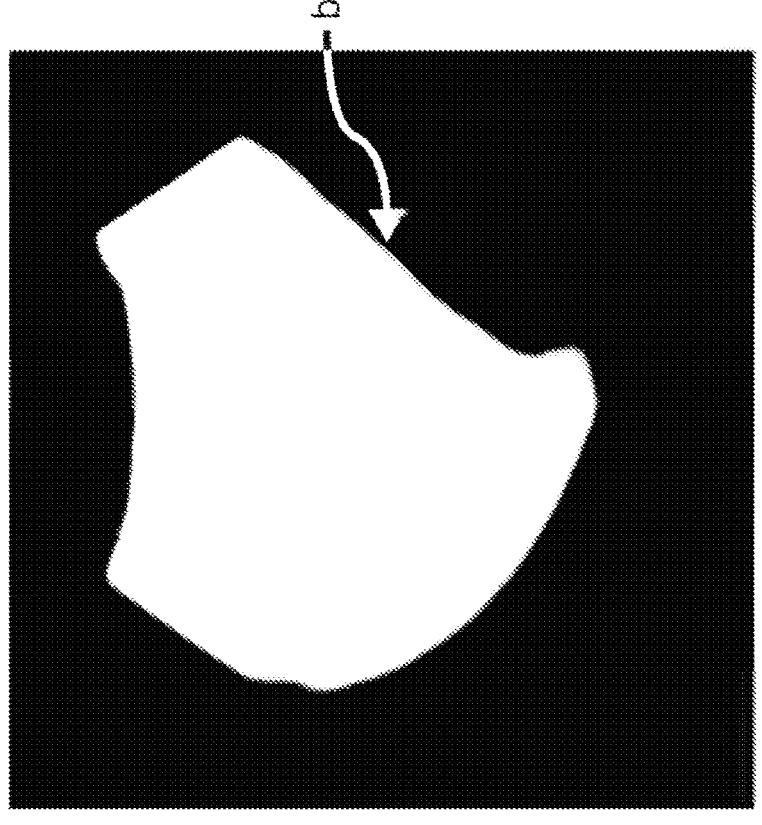
FIG. 6B illustrates the output segmentation result from the processing of the image of FIG. 6A.
Figure 6A:
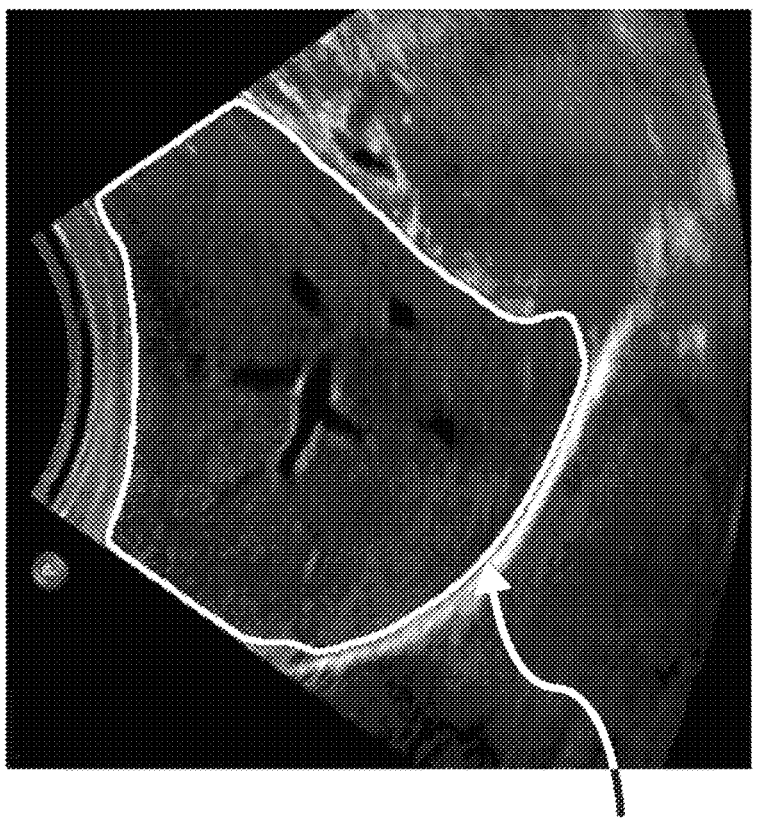
FIG. 6A illustrates an original ultrasound image of a liver.
Figures 7A, 7B:
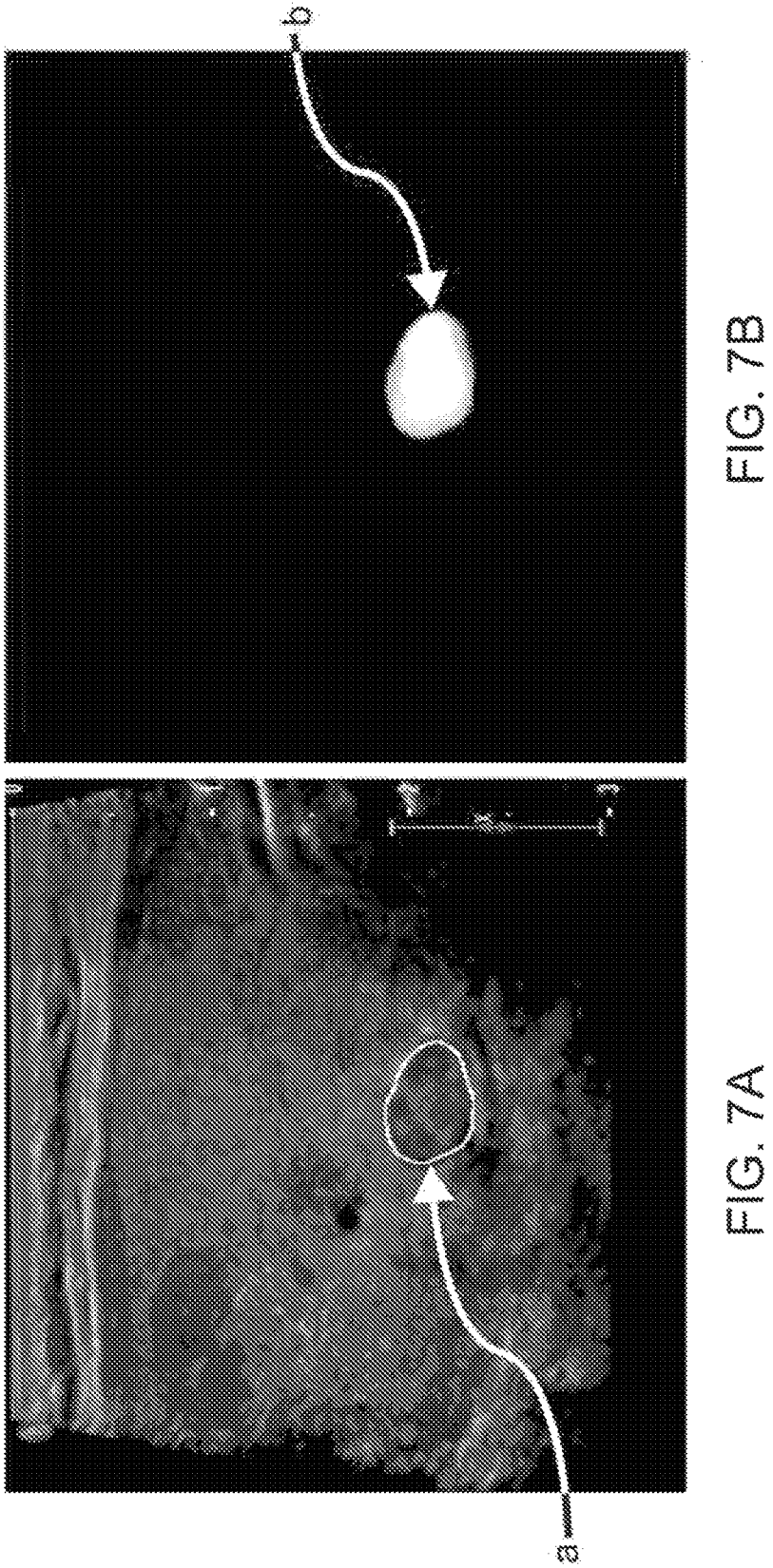
FIG. 7A illustrates an original ultrasound image of a thyroid.
FIG. 7B illustrates the output segmentation result from the processing of the image of FIG. 7A.

FIG. 6A shows an original ultrasound image of a liver; FIG. 6B is the processed output segmentation result. FIG. 7A shows an original ultrasound image of thyroid nodules; FIG. 7B is the processed output segmentation result.

The region enclosed by the white contour (a) defines the boundary of the segmented part and the corresponding segmentation mask (the output of $U^2$-net) is shown in the right panel (b).

Figure 8:
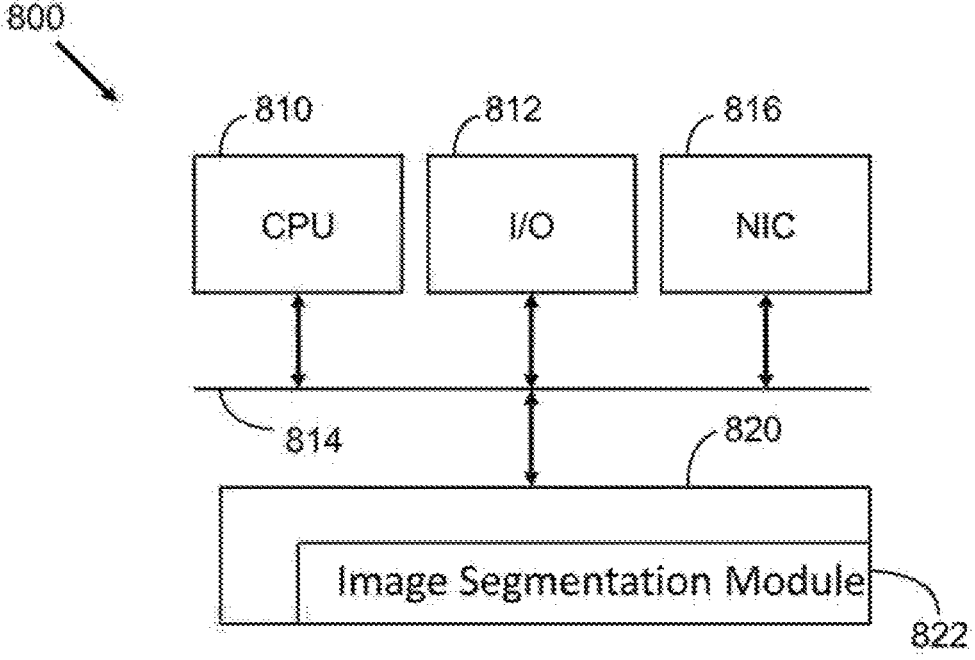
FIG. 8 illustrates a computer configured in accordance with an embodiment of the invention.

FIG. 8 illustrates a machine 800 configured to implement the disclosed processing operations. A processor 810 is connected to input/output devices 812 via a bus 814. A network interface circuit 816 is also connected to the bus 814 to provide connectivity to a network (not shown). A memory 820 is also connected to the bus 814. The memory 820 stores an image segmentation module 822 with instructions executed by processor 810 to implement the processing operations disclosed herein.

An embodiment of the present invention relates to a computer storage product with a computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs, DVDs and holographic devices; magneto-optical media; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, or other object-oriented programming language and development tools. Another embodiment of the invention may be implemented in hard-wired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A non-transitory computer readable storage medium with instructions which, when executed by a processor, cause the processor to:

receive an image;

apply the image to a sequence of encoders that includes a first encoder and one or more subsequent encoders, wherein each encoder in the sequence of encoders comprises a U network encoder which performs convolution neural network processing in an orthogonal dimension, and the one or more subsequent encoders receive a down-sampled version of the image from a prior encoder, the sequence of encoders forming a first dimension orthogonal to the orthogonal dimension;

apply a result of the sequence of encoders to a sequence of decoders that includes a first decoder and one or more subsequent decoders, wherein a respective decoder in the one or more subsequent decoders comprises a U network decoder that performs convolution neural network processing of an up-sampled version of the image from the first decoder, and the sequence of decoders forms a second dimension parallel to the first dimension;

produce probability outputs from paired encoders and decoders in the sequence of encoders and the sequence of decoders; and combine the probability outputs to form a final output.

2. The non-transitory computer readable storage medium of claim 1, wherein the instructions further cause a respective encoder in the sequence of encoders and a respective decoder in the sequence of decoders to receive input feature maps and generate multi-scale features and local features.

3. The non-transitory computer readable storage medium of claim 1, wherein the image has a shape with an associated height, width, and input channel number.

4. The non-transitory computer readable storage medium of claim 3, wherein the final output is characterized as $Y_{output}=K(W,X_{input})$, wherein $X_{input}$ is the image, $Y_{output}$ is a probability map with pixel values ranging from zero to one with the shape of the associated height and width, and W denotes weights of kernel filters.

5. The non-transitory computer readable storage medium of claim 1, wherein the final output is a multi-channel feature map fed to an activation function to produce multi-class segmentation results.

6. The non-transitory computer readable storage medium of claim 1, wherein the final output is characterized as a feature map with regression results without using activation functions.

7. The non-transitory computer readable storage medium of claim 3, wherein the input channel number is two or more.

8. The non-transitory computer readable storage medium of claim 1, wherein a respective encoder in the sequence of encoders and a respective decoder in the sequence of decoders have configurable heights.

9. The non-transitory computer readable storage medium of claim 1, wherein a respective encoder in the sequence of encoders and a respective decoder in the sequence of decoders have configurable filter numbers.

10. The non-transitory computer readable storage medium of claim 1, wherein each decoder in the one or more subsequent decoders concatenates an up-sampled feature map from a previous decoder with a down-sampled feature from a paired encoder.

11. The non-transitory computer readable storage medium of claim 1, wherein the instructions to combine the probability outputs include instructions which, when executed by the processor, cause the processor to:

concatenate the probability outputs to form concatenated probability outputs.

12. The non-transitory computer readable storage medium of claim 11, wherein the instructions further cause the processor to:

apply a convolution layer to the concatenated probability outputs to form convoluted concatenated probability outputs.

13. The non-transitory computer readable storage medium of claim 12, wherein the instructions further cause the processor to apply a sigmoid function to the convoluted concatenated probability outputs to form the final output.

14. A method, comprising:

at a computer system that includes a processor and memory:

receiving an image;

applying the image to a sequence of encoders that includes a first encoder and one or more subsequent encoders, wherein each encoder in the sequence of encoders comprises a U network encoder which performs convolution neural network processing in an orthogonal dimension, and the one or more subsequent encoders receive a down-sampled version of the image from a prior encoder, the sequence of encoders forming a first dimension orthogonal to the orthogonal dimension;

applying a result of the sequence of encoders to a sequence of decoders that includes a first decoder and one or more subsequent decoders, wherein a respective decoder in the one or more subsequent decoders comprises a U network decoder that performs convolution neural network processing of an up-sampled version of the image from the first decoder, and the sequence of decoders forms a second dimension parallel to the first dimension;

producing probability outputs from paired encoders and decoders in the sequence of encoders and the sequence of decoders; and combining the probability outputs to form a final output.

15. The method of claim 14, further comprising:

causing a respective encoder in the sequence of encoders and a respective decoder in the sequence of decoders to receive input feature maps and generate multi-scale features and local features.

16. The method of claim 15, wherein the image has a shape with an associated height, width, and input channel number.

17. The method of claim 16, wherein the final output is characterized as $Y_{output}=K(W,X_{input})$, wherein $X_{input}$ is the image, $Y_{output}$ is a probability map with pixel values ranging from zero to one with the shape of the associated height and width, and W denotes weights of kernel filters.

18. The method of claim 14, wherein the final output is a multi-channel feature map fed to an activation function to produce multi-class segmentation results.

19. A computer system, comprising:

a processor; and memory storing one or more programs, the one or more programs including instructions for:

receiving an image;

applying the image to a sequence of encoders that includes a first encoder and one or more subsequent encoders, wherein each encoder in the sequence of encoders comprises a U network encoder which performs convolution neural network processing in an orthogonal dimension, and the one or more subsequent encoders receive a down-sampled version of the image from a prior encoder, the sequence of encoders forming a first dimension orthogonal to the orthogonal dimension;

applying a result of the sequence of encoders to a sequence of decoders that includes a first decoder and one or more subsequent decoders, wherein a respective decoder in the one or more subsequent decoders comprises a U network decoder that performs convolution neural network processing of an up-sampled version of the image from the first decoder, and the sequence of decoders forms a second dimension parallel to the first dimension;

producing probability outputs from paired encoders and decoders in the sequence of encoders and the sequence of decoders; and combining the probability outputs to form a final output.

20. The computer system of claim 19, wherein the memory further includes for causing a respective encoder in the sequence of encoders and a respective decoder in the sequence of decoders to receive input feature maps and generate multi-scale features and local features.

\* \* \* \* \*